United States Patent [19]

Shinar et al.

[11] Patent Number: 5,620,008
[45] Date of Patent: Apr. 15, 1997

[54] FLUID COUPLING DEVICE FOR A BLOOD SAMPLING UNIT

[75] Inventors: Eilat Shinar, Zion; Eli Shemesh, Ashdod; Sarit Rotem, Givatayim; Menashe Choori, Hod Hasharon; Ellen Tobe, Tel Aviv, all of Israel

[73] Assignee: Migada Inc., Englewood Cliffs, N.J.

[21] Appl. No.: 356,290

[22] PCT Filed: Apr. 21, 1993

[86] PCT No.: PCT/US93/03787

§ 371 Date: Apr. 13, 1995

§ 102(e) Date: Apr. 13, 1995

[87] PCT Pub. No.: WO93/21821

PCT Pub. Date: Nov. 11, 1993

[30] Foreign Application Priority Data

Apr. 23, 1992 [IL] Israel .......................................... 101680

[51] Int. Cl.$^6$ ........................................................ A61B 5/00
[52] U.S. Cl. ........................... 128/764; 604/283; 604/412; 604/414
[58] Field of Search .................................... 604/283, 905, 604/411–414; 128/760, 763, 764

[56] References Cited

U.S. PATENT DOCUMENTS

| | | |
|---|---|---|
| 3,877,465 | 4/1975 | Miyake . |
| 4,326,518 | 4/1982 | Williams . |
| 4,607,671 | 8/1986 | Aalto et al. . |
| 4,763,648 | 8/1988 | Wyatt . |
| 4,790,827 | 12/1988 | Haber et al. . |
| 4,920,970 | 5/1990 | Wyatt . |
| 4,935,012 | 6/1990 | Magre et al. . |
| 4,946,445 | 8/1990 | Lynn . |
| 4,981,140 | 1/1991 | Wyatt . |
| 5,002,066 | 3/1991 | Simpson et al. . |
| 5,045,081 | 9/1991 | Dysarz . |
| 5,084,034 | 1/1992 | Zanotti . |
| 5,201,717 | 4/1993 | Wyatt et al. ............................ 604/192 |
| 5,385,547 | 1/1995 | Wong et al. ............................ 604/87 |

FOREIGN PATENT DOCUMENTS

| | | |
|---|---|---|
| 351643 | 1/1990 | European Pat. Off. . |
| 356002 | 2/1990 | European Pat. Off. . |
| 423335 | 4/1991 | European Pat. Off. . |
| 428723 | 5/1991 | European Pat. Off. . |
| 462814 | 12/1991 | European Pat. Off. . |
| 31211 | 12/1968 | Israel . |
| 89/04141 | 5/1989 | WIPO . |
| 89/04678 | 6/1989 | WIPO . |
| 89/11304 | 11/1989 | WIPO . |
| 90/02515 | 3/1990 | WIPO . |
| 9012606 | 11/1990 | WIPO . |
| 9100115 | 1/1991 | WIPO . |

OTHER PUBLICATIONS

Patent Abstracts of Japan, vol. 13, No. 414 (C–635), 13 Sep. 1989 & JP–A–01 151464 (Terumo Corp.) 14 Jun. 1989.

*Primary Examiner*—Corrine M. McDermott
*Attorney, Agent, or Firm*—Helfgott & Karas, PC.

[57] ABSTRACT

A blood sampling system includes a blood collecting assembly having an in-line blood sampling unit, a blood sampling container, and a fluid coupling device coupled to the in-line blood sampling unit for coupling the in-line blood sampling unit to the blood sampling container. The fluid coupling device has a housing having an anterior section formed with an open end capable of being applied to the blood sampling unit, a posterior section formed with an open end capable of receiving the blood sampling container, and a transversely-extending member between the anterior and posterior sections. A needle is secured to the transversely-extending member so as to extend axially of the housing. The needle has anterior and posterior sections extending within the anterior and posterior sections of the housing, respectively, both the anterior and posterior sections of the needle terminating sufficiently short of the open ends of the anterior and posterior sections of the housing to be protected against accidentally puncturing a user's skin. Attaching slots are formed on the housing for attaching the housing to the blood sampling unit with the anterior section of the needle penetrating the blood sampling unit perpendicularly to the flow of blood therethrough.

7 Claims, 3 Drawing Sheets

FLUID COUPLING DEVICE FOR A BLOOD SAMPLING UNIT

The present invention relates to a fluid coupling device, and particularly to such a device for coupling an in-line blood sampling unit of a blood collecting assembly to a blood sampling container.

One known technique for drawing samples of blood uses a double-ended needle, one end of which is to be inserted into the subject's blood vessel, and the opposite end of which is to be coupled to a blood collecting container under vacuum such as to draw the blood into the container. Examples of this type of device are described in European Patent Application 88906129.7 and U.S. Pat. Nos. 3,877,465 and 4,935,012.

It is also known to draw a sample of blood via an in-line blood sampling unit already in place for another purpose. For example, where a blood collecting assembly is already connected to a subject donating blood, it may be desirable to extract a sample of the blood for diagnostic or testing purposes. This may be done by providing the blood collecting assembly with an in-line blood sampling unit, as described, for example, in U.S. Pat. Nos. 4,763,648, 4,920,970 and 4,981,140.

According to the present invention, there is provided a fluid coupling device for coupling an in-line blood sampling unit of a blood collecting assembly to a blood sampling container, comprising: a housing having an anterior section formed with an open end capable of being applied to the blood sampling device, a posterior section integral with said anterior section and formed with an open end capable of receiving the blood sampling container, and a transversely-extending member between the anterior and posterior sections; a needle secured to the transversely-extending member so as to extend axially of the housing; the needle having anterior and posterior sections extending within the anterior and posterior sections of the housing, respectively; both the anterior and posterior sections of the needle terminating sufficiently short of the open ends of the anterior and posterior sections of the housing such a to be protected against accidentally puncturing a user's skin; and attaching means for attaching the housing to the blood sampling device with the anterior section of the needle penetrating the blood sampling unit perpendicularly to the flow of blood therethrough.

According to further features in the described preferred embodiment, the attaching means comprises a pair of bayonet-type slots formed in the opposite sides of the housing anterior section, each slot having an axially-extending portion starting from the open end of the housing anterior section and terminating in a circumferentially-extending portion inwardly of the open end.

Further features and advantages of the invention will be apparent from the description below.

The invention is herein described, by way of example only, with reference to the accompanying drawings, wherein.

Figure 1:
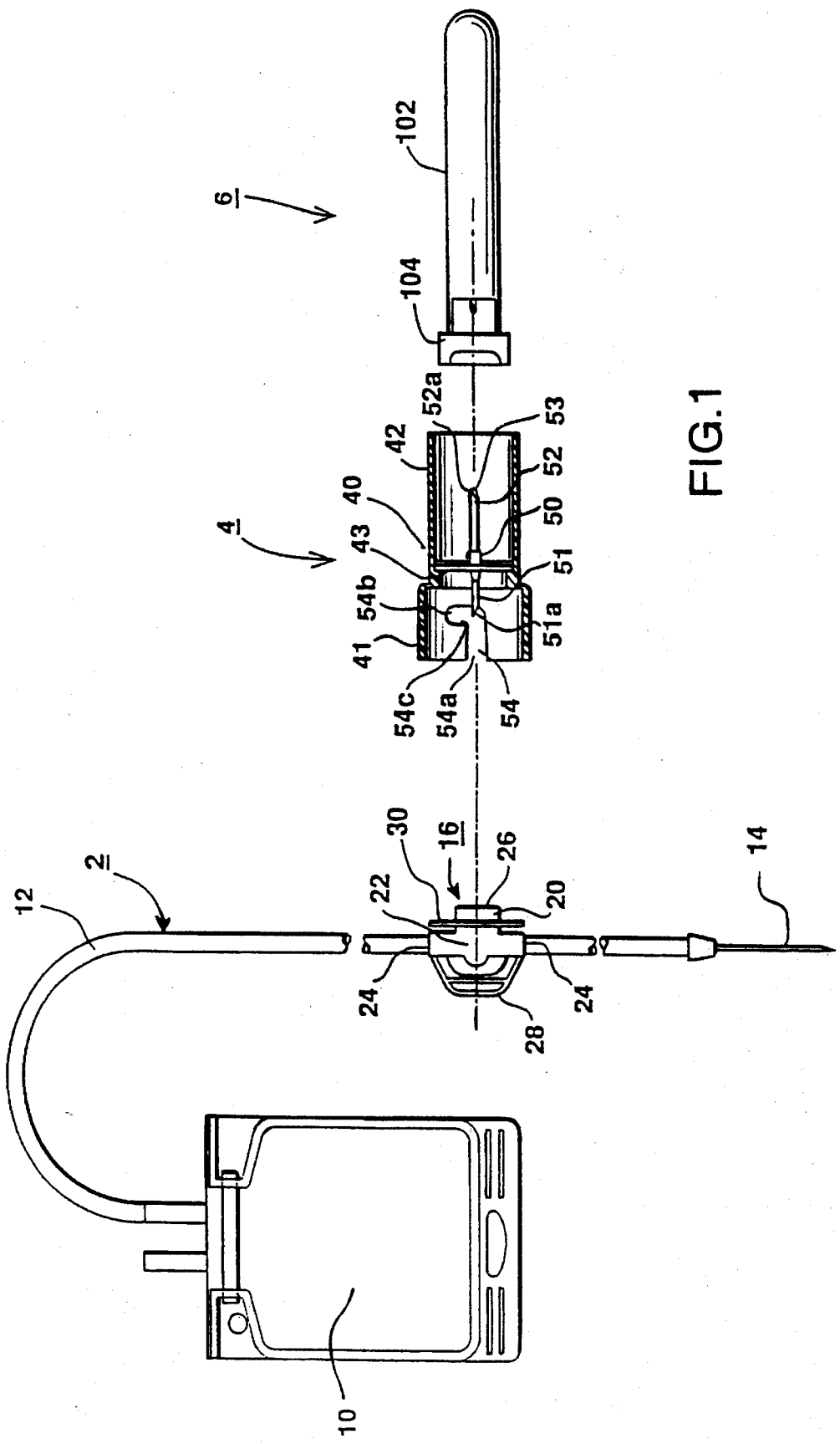
FIG. 1 illustrates a blood sampling system including one form of fluid coupling device constructed in accordance with the present invention.
Figure 3:
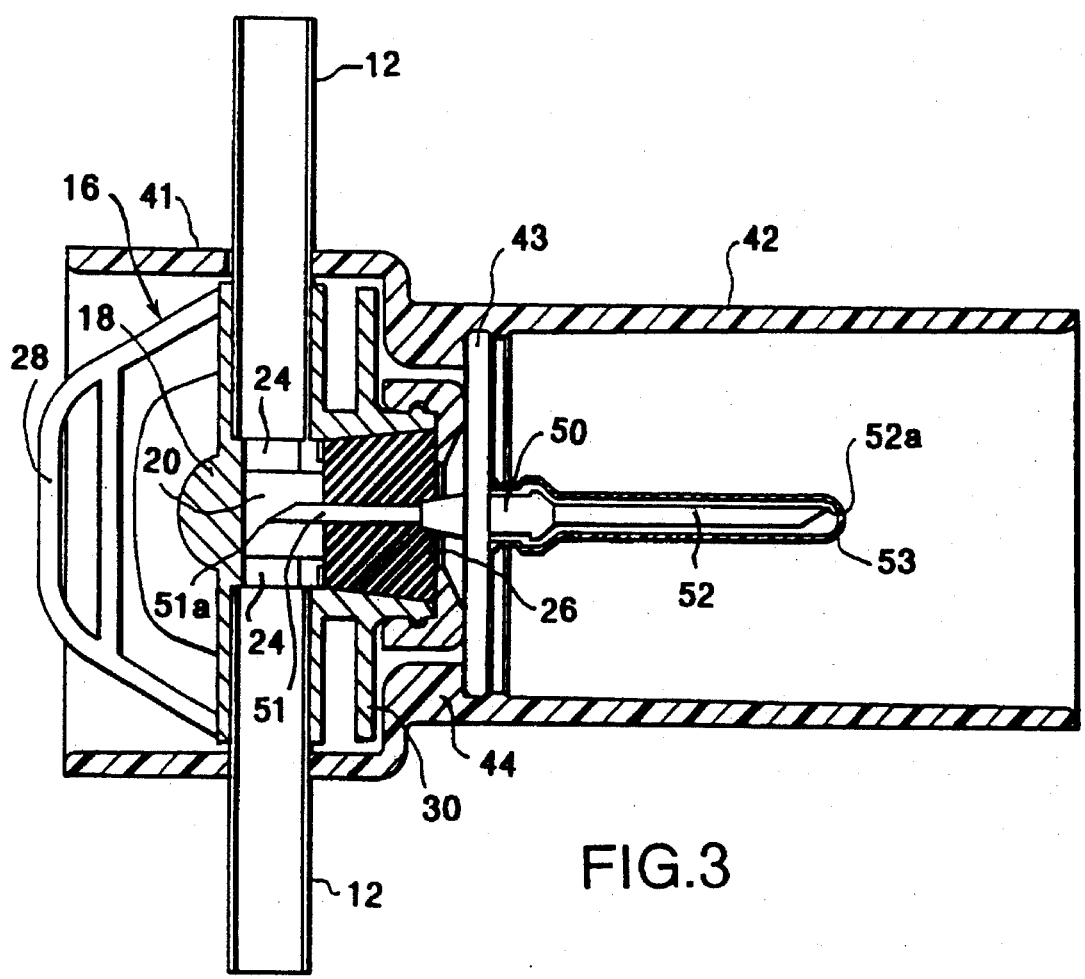
FIG. 3 illustrates the attachment of the fluid coupling device of FIG. 2 to the in-line blood sampling unit of the blood collecting assembly of FIG. 1.

The blood sampling system illustrated in FIG. 1 comprises an in-line blood sampling assembly 2, a fluid coupling device 4, and a blood sampling container 6. The in-line blood collecting assembly may be of a known construction, such as described in the above-cited U.S. Pat. Nos. 4,763,648, 4,902,970 and 4,981,140, as illustrated in FIG. 3. The blood sampling container 6 may also be of a known construction. The present invention relates primarily to the fluid coupling device 4 for coupling the in-line blood collecting assembly 2 to the blood sampling container 6 so as to allow a sample of blood to be drawn into the latter container at the same time blood is being drawn from the subject into a blood collection bag 10 of the blood collecting assembly 2.

The blood collection bag 10 of assembly 2 is connected by a tube 12 to a needle 14 adapted to be inserted into the subject's blood vessel. Assembly 2 includes an in-line blood sampling unit 16 introduced into tube 12 at a convenient location between needle 14 and the collection bag 10, and enables a needle (which term also includes a cannula) to be inserted into the unit to draw out a sample of the blood flowing therethrough. As described in the above-cited U.S. patents and as illustrated in FIG. 3, unit 16 includes a housing 18 formed with a chamber 20 having two ports 24 receiving the ends of two tubes 12. Chamber 20 is provided with a plug or septum 26 which seals the interior of that chamber relative to the atmosphere, but which is penetratable by a needle (or cannula) to gain access to chamber 20 through which the blood flows. Unit 16 further includes a finger-gripping tab 28 for gripping the unit between the thumb and a finger of the user, and a disc 30 for centering and guiding the fluid coupling device when inserted into the in-line sampling unit 16.

Figure 2:
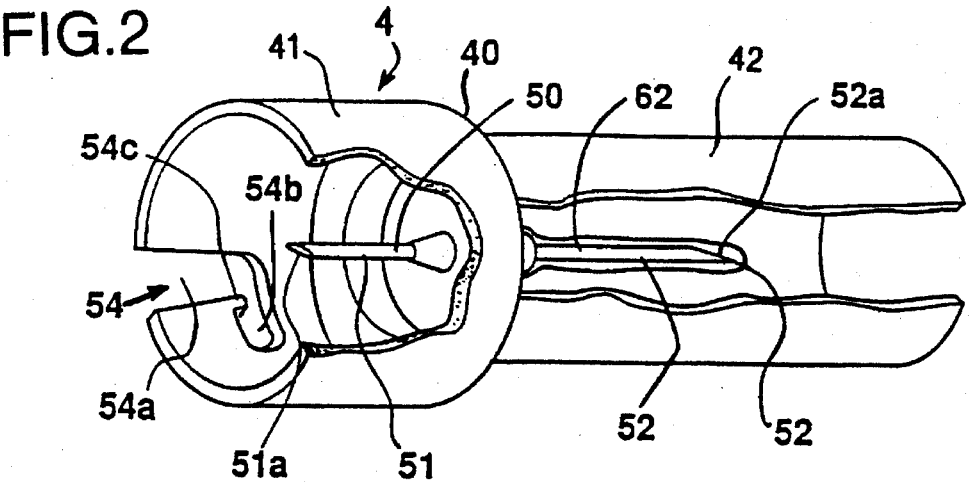
FIG. 2 is a three-dimensional view, partly broken away to show internal structure, of the fluid coupling device illustrated in FIG. 1.

The fluid coupling device 4 in FIG. 1 is more particularly illustrated in FIGS. 2 and 3. It includes a housing 40 having an anterior section 41 formed with an open end capable of being applied to the blood sampling unit 16, and a posterior section 42 also formed with an open end for receiving the blood sampling container 6 (FIG. 1). Housing 40 further includes a transversely-extending member 43 in the form of a transverse wall dividing the interior of housing 40 into the anterior section 41 and posterior section 42. Housing 40 is of cylindrical configuration. Its anterior section 41 is of larger diameter than its posterior section 42. The juncture 44 between the two sections, to which the transverse wall 43 is fixed, is of increased thickness for rigidly supporting the transverse wall and a needle 50 secured to transverse wall 43 so as to extend axially of the housing 40.

Needle 50 includes an anterior section 51 extending within the anterior section 41 of housing 40, and a posterior section 52 extending within the posterior section 42 of the housing. Needle 50 is made of metal, and both its sections terminate in sharpened tips 51a, 52a, respectively. Preferably, the posterior section 52 is enclosed within a protective sheath 53, such as of a thin latex material, which can be penetrated when the sharpened tip 52a of needle section 52 is applied to the blood collecting container 6 (FIG. 1). Both the anterior section 51 and the posterior section 52 of needle 50 terminate well short of the open ends of the anterior and posterior sections 41, 42, respectively, so as to be protected against accidentally puncturing the user's skin.

Fluid coupling device 4 further includes attaching means for attaching the anterior end 41 of its housing 40 to the blood sampling unit 16, with the anterior section 51 of the needle 50 penetrating the blood sampling unit perpendicularly to the tube 12 through which the blood flows. Such attaching means comprises a pair of bayonet-type slots 54 formed in the opposite sides of the housing anterior section 41. Each slot has an axially-extending portion 54a starting from the open end of the housing anterior section 41, and terminating in a circumferentially-extending portion 54b inwardly of the open end of section 41. A projection 54c at the juncture between the two slot portions 54a, 54b, produces an audible "click" when the housing is applied to the blood sampling unit 16 and is locked thereon, as will be described below.

The blood sampling container 6 is preferably of the Vacutainer (Reg. T.M.) type and includes a test tube 102 having a rubber plug 104 over its open end. The central portion of rubber plug 104 is penetrated by the posterior section 52 of the needle when the container is pushed into the open end of the housing posterior section 42.

The manner of using the blood sampling system illustrated in FIGS. 1–3 will be apparent from the above description. Thus, after the blood collecting assembly 2 has been applied to the subject, with the needle 14 inserted into the subject's blood vessel to draw blood via tube 12 into the collection bag 10, the coupling device 4 may be attached to the in-line blood sampling unit 16. This is done by aligning slot portions 54a of the bayonet slots 54 with the ends of the tube 12 on opposite sides of the blood sampling unit 16, pressing housing 40 to move slot portions 54a over the tubes, and then slightly rotating housing 40 to move the tubes into slot portions 54b. As the tubes pass projections 54c at the juctures of slot portions 54a and 54b, a "click" is heard, thereby informing the user that the fluid coupling housing 40 is locked onto the blood sampling unit 16.

During this insertion of the fluid coupling device 4, anterior section 51 of the needle 50 penetrates the plug 26 of the blood sampling unit 16, so that the tip of needle section 51 is in communication with the blood flowing through chamber 20 of unit 16.

Sheath 53 over the posterior section 52 of the needle prevents leakage of blood at this time. The blood sampling container 6 may then be inserted into the posterior section 42 of housing 40, causing the sharpened tip 52a of the posterior needle section 52 to penetrate the sheath 53 and also the rubber plug 104 of the blood sampling container 6. When container 6 is removed, sheath 53 reseals the tip of the posterior needle section 52.

Figure 4:
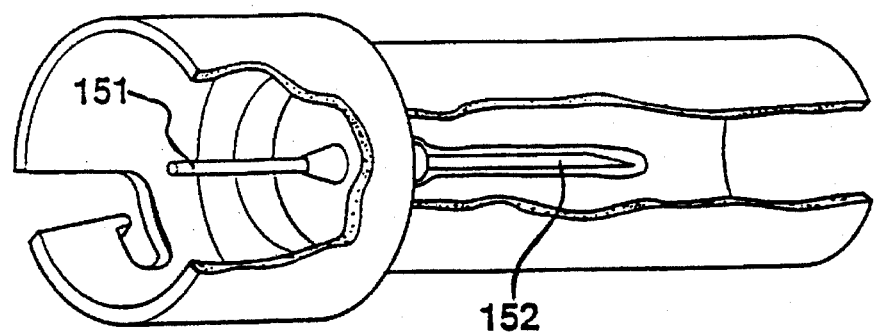
FIG. 4 is a view similar to that of FIG. 2 but illustrating another form of fluid coupling device constructed in accordance with the present invention.

FIG. 4 illustrates a variation wherein the anterior needle section, therein designated 151, is formed with a blunt tip, 151a, rather than with a sharpened tip. In such case, the plug 26 (FIG. 1) in the blood sampling unit 16 should be preslit to enable the blunt needle to penetrate it, and also to become resealed when the blunt needle is withdrawn from it. Preferably, when using a blunt tip needle as illustrated in FIG. 4, the anterior section 151 of the needle is made of a plastic material, whereas the posterior section 152 of the needle is made of metal. In all other respects, the fluid coupling device illustrated in FIG. 4 is constructed, and is used, in the same manner as described above with respect to FIGS. 1–3.

Figure 5:
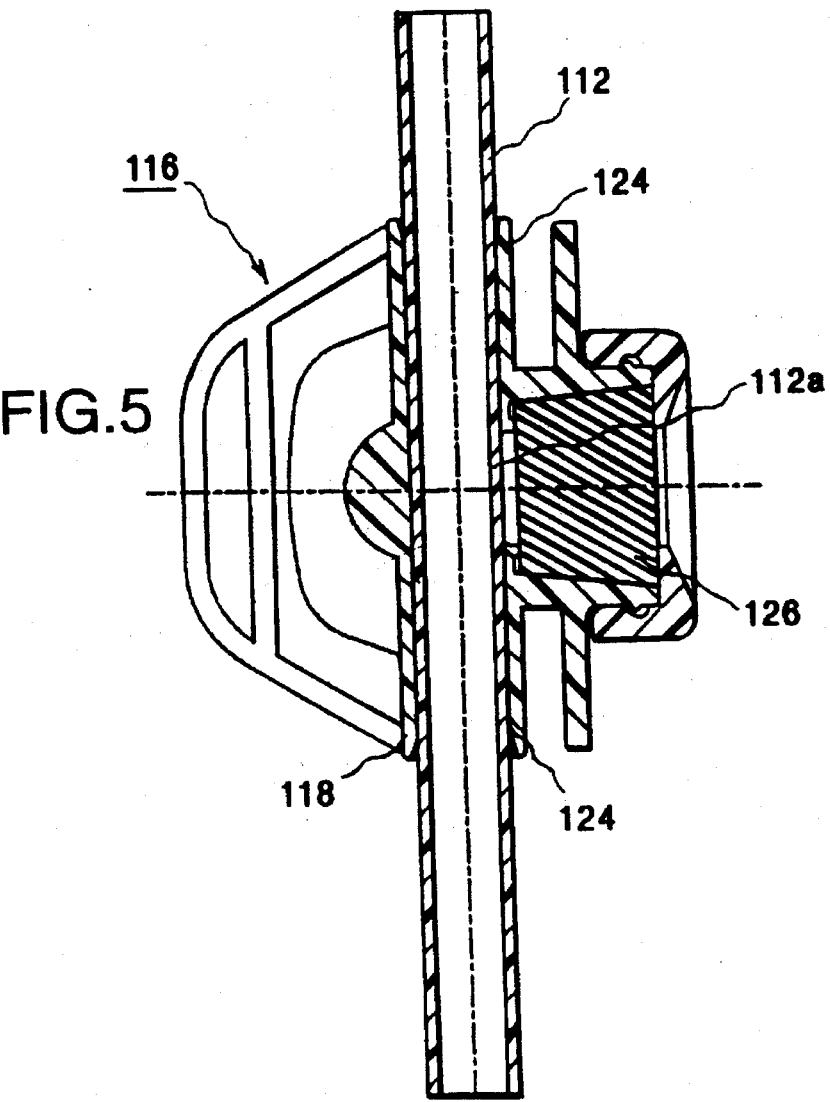
FIG. 5 illustrates a modification in the construction of the in-line blood sampling unit.

FIG. 5 illustrates a variation in the consturction of the in-line blood sampling unit, therein designated 116, wherein a continuous tube 112 is forced through the two ports 124 of the housing 118, and the plug 126 is aligned with portion 112a of the tube located within the housing between its two ports, such that tube portion 112a would also be penetrated by the anterior section of the needle when penetrating plug 126 of the blood sampling unit 116.

What is claimed is:

1. A blood sampling system comprising:

a blood collecting assembly having an in-line blood sampling unit:

a blood sampling container; and a fluid coupling device coupled to said in-line blood sampling unit for coupling said in-line blood sampling unit to said blood sampling container, said fluid coupling device comprising:

a housing having an anterior section formed with an open end capable of being applied to the blood sampling unit, a posterior section formed with an open end capable of receiving the blood sampling container, and a transversely-extending member between said anterior and posterior sections;

a needle secured to said transversely-extending member so as to extend axially of said housing; said needle having anterior and posterior sections extending within said anterior and posterior sections of the housing, respectively; both the anterior and posterior sections of the needle terminating sufficiently short of the open ends of the anterior and posterior sections of the housing such as to be protected against accidentally puncturing a user's skin; and attaching means formed on said housing for attaching said housing to the blood sampling unit with the anterior section of the needle penetrating the blood sampling unit perpendicularly to the flow of blood therethrough;

wherein said in-line sampling unit includes a sampling unit housing having two ports, a tube threaded through the housing such that a portion of the tube is located within said sampling unit housing between said two ports, and a plug closing said sampling unit housing and aligned with the portion of the tube located within the sampling unit housing between said two ports, such that said portion of the tube is penetrated by the anterior section of the needle when penetrating the blood sampling unit.

2. The system according to claim 1, wherein said attaching means comprises a pair of bayonet-type slots formed at opposite sides of the anterior section of the housing of said fluid coupling device, each slot having an axially-extending portion starting from the open end of said anterior section of the housing and terminating in a circumferentially-extending portion inwardly of said open end.

3. The system according to claim 1, wherein said transversely-extending member is a transverse wall dividing the interior of the housing into said anterior and posterior sections.

4. The system according to claim 3, wherein the anterior section of the housing is of larger diameter than the posterior section of the housing.

5. The system according to claim 1, wherein said housing is of cylindrical configuration.

6. The system according to claim 1, wherein said posterior section of the needle has a sharpened tip and is covered by a protective sheath which is penetrated by said sharpened tip when the fluid coupling device receives the blood sampling container.

7. The system according to claim 1, wherein the anterior section of the needle has a sharpened tip to penetrate the plug of the in-line blood sampling unit when attached thereto.

* * * * *